US011141255B2

(12) United States Patent
Beaudette

(10) Patent No.: US 11,141,255 B2
(45) Date of Patent: Oct. 12, 2021

(54) INTRODUCER FOR URINARY INCONTINENCE

(71) Applicant: Rinovum Subsidiary 2, LLC, Monroeville, PA (US)

(72) Inventor: Sean Beaudette, Pittsburgh, PA (US)

(73) Assignee: OVALA, INC., Monroeville, PA (US)

( * ) Notice: Subject to any disclaimer, the term of this patent is extended or adjusted under 35 U.S.C. 154(b) by 463 days.

(21) Appl. No.: 15/963,616

(22) Filed: Apr. 26, 2018

(65) Prior Publication Data
US 2019/0038389 A1 Feb. 7, 2019

Related U.S. Application Data

(60) Provisional application No. 62/490,364, filed on Apr. 26, 2017.

(51) Int. Cl.
*A61F 13/26* (2006.01)
*A61B 17/00* (2006.01)
*A61F 2/00* (2006.01)

(52) U.S. Cl.
CPC ............ *A61F 2/0022* (2013.01); *A61F 2/005* (2013.01); *A61F 2/0009* (2013.01); *A61F 13/266* (2013.01); *A61B 2017/00805* (2013.01)

(58) Field of Classification Search
CPC ........ A61F 13/15; A61F 13/26; A61F 13/266; A61F 2/0022; A61F 2/0036; A61F 2/004; A61F 2/005; A61F 2/009; A61F 6/08; A61F 6/12; A61F 6/14; A61F 6/18; A61B 2017/00805; A61K 9/0034
See application file for complete search history.

(56) References Cited

U.S. PATENT DOCUMENTS

| 3,196,873 | A | | 7/1965 | Bletzinger et al. |
| 4,428,370 | A | | 1/1984 | Keely |
| 4,536,178 | A | | 8/1985 | Lichstein et al. |
| 4,592,740 | A | * | 6/1986 | Mahruki ................. A61F 13/26 |
| | | | | 128/838 |
| 4,726,805 | A | | 2/1988 | Sanders, III |
| 4,846,819 | A | | 7/1989 | Welch |
| 5,036,867 | A | | 8/1991 | Biswas |
| 5,256,133 | A | | 10/1993 | Spitz |
| 5,370,633 | A | | 12/1994 | Viiiaita |
| 5,437,628 | A | | 8/1995 | Fox et al. |
| 5,671,755 | A | | 9/1997 | Simon et al. |
| 5,771,899 | A | | 6/1998 | Martelly et al. |

(Continued)

*Primary Examiner* — Benjamin J Klein
*Assistant Examiner* — Heather K Barnwell
(74) *Attorney, Agent, or Firm* — Welsh Flaxman & Gitler LLC

(57) ABSTRACT

An introducer used to insert a urinary incontinence device into a vagina. The introducer includes a housing including a vaginal insertion tube at a proximal end of the housing and a storage section at a distal end of the housing. The storage section is shaped and dimensioned for storage of the urinary incontinence device prior to insertion and the vaginal insertion tube is shaped and dimensioned for the passage of the urinary incontinence device therethrough. The dimensions of the storage section are such that the urinary incontinence device contained therein is in its deployed non-compressed state allowing the urinary incontinence device to be stored in its non-compressed state prior to use. The introducer also includes a plunger which travels within the housing.

22 Claims, 11 Drawing Sheets

(56) References Cited

U.S. PATENT DOCUMENTS

| | | |
|---|---|---|
| 5,785,640 A | 7/1998 | Kresch et al. |
| 6,090,098 A | 7/2000 | Zunker et al. |
| 6,142,928 A | 11/2000 | Zunker et al. |
| 6,413,206 B2 | 7/2002 | Biswas |
| 6,418,930 B1 | 7/2002 | Fowler |
| 6,460,542 B1 | 10/2002 | James |
| 6,645,136 B1 | 11/2003 | Zunker et al. |
| 6,645,137 B2 | 11/2003 | Ulmsten et al. |
| 6,652,477 B2 | 11/2003 | Karapasha et al. |
| 6,676,594 B1 | 1/2004 | Zunker et al. |
| 6,695,763 B2 | 2/2004 | Zunker et al. |
| 6,808,485 B2 | 10/2004 | Zunker |
| 6,939,289 B2 | 9/2005 | Zunker et al. |
| 7,263,999 B2 | 9/2007 | Kaseki et al. |
| 7,351,195 B2 | 4/2008 | Farrell |
| 7,628,156 B2 | 12/2009 | Astani et al. |
| 7,717,892 B2 | 5/2010 | Bartning et al. |
| 7,736,298 B2 | 6/2010 | Guerquin et al. |
| 7,771,344 B2 | 8/2010 | Ziv |
| 7,892,163 B2 | 2/2011 | Bartning et al. |
| 7,935,098 B2 | 5/2011 | Bartning et al. |
| 7,942,806 B2 | 5/2011 | Tracey et al. |
| 7,981,021 B2 | 7/2011 | Spitz et al. |
| 7,981,024 B2 | 7/2011 | Levy |
| 8,047,980 B2 | 11/2011 | Bartning et al. |
| 8,127,768 B2 | 3/2012 | Ziv |
| 8,177,706 B2 | 5/2012 | Bartning et al. |
| 8,221,374 B2 | 7/2012 | Hou et al. |
| 8,302,608 B2 | 11/2012 | Harmanli |
| 8,323,176 B2 | 12/2012 | Spitz et al. |
| 8,435,168 B2 | 5/2013 | Ziv et al. |
| 8,608,639 B2 | 12/2013 | Bartning et al. |
| 8,613,698 B2 | 12/2013 | Bartning et al. |
| 8,617,047 B2 | 12/2013 | Sinai et al. |
| 8,651,109 B2 | 2/2014 | Ziv et al. |
| 8,652,026 B2 | 2/2014 | Zunker et al. |
| 8,652,027 B2 | 2/2014 | Hou et al. |
| 8,753,258 B2 | 6/2014 | Bartning et al. |
| 8,911,344 B2 | 12/2014 | Altan et al. |
| 8,911,345 B2 | 12/2014 | Ziv et al. |
| 8,920,302 B2 | 12/2014 | Levy |
| 8,923,493 B2 | 12/2014 | Hillis et al. |
| 9,022,919 B2 | 5/2015 | Ellefson et al. |
| 9,050,183 B2 | 6/2015 | Bartning et al. |
| 9,078,726 B2 | 7/2015 | Karapasha |
| 9,173,768 B2 | 11/2015 | Bartning et al. |
| 9,198,748 B2 | 12/2015 | Ziv et al. |
| 9,320,640 B2 | 4/2016 | Durling |
| 9,339,361 B2 | 5/2016 | Ziv et al. |
| 9,339,363 B2 | 5/2016 | Ziv et al. |
| 9,339,364 B2 | 5/2016 | Durling et al. |
| 9,393,090 B2 | 7/2016 | Karapasha |
| 9,398,984 B2 | 7/2016 | Hou et al. |
| 9,408,685 B2 | 8/2016 | Hou et al. |
| 9,439,748 B2 | 9/2016 | Durling et al. |
| 9,549,798 B2 | 1/2017 | Sinai et al. |
| 9,597,222 B2 | 3/2017 | Durling et al. |
| 9,655,769 B2 | 5/2017 | Ziv et al. |
| 2002/0083949 A1 | 7/2002 | James |
| 2005/0113228 A1 | 5/2005 | Marcotte |
| 2007/0203429 A1 | 8/2007 | Ziv |
| 2008/0033230 A1 | 2/2008 | Bartning et al. |
| 2008/0243046 A1* | 10/2008 | Cettina ............... A61F 13/266 604/15 |
| 2008/0281149 A1 | 11/2008 | Sinai et al. |
| 2009/0247929 A1 | 10/2009 | Hou et al. |
| 2009/0247930 A1* | 10/2009 | Fung .................. A61F 13/266 604/16 |
| 2009/0318750 A1 | 12/2009 | Ziv et al. |
| 2010/0197997 A1* | 8/2010 | Hou ..................... A61F 2/005 600/29 |
| 2011/0275977 A1 | 11/2011 | Watanabe et al. |
| 2012/0136199 A1 | 5/2012 | Hou et al. |
| 2012/0259162 A1 | 10/2012 | Karapasha |
| 2012/0259166 A1 | 10/2012 | Karapasha |
| 2012/0259167 A1 | 10/2012 | Karapasha et al. |
| 2012/0271098 A1 | 10/2012 | Ziv et al. |
| 2013/0014762 A1* | 1/2013 | Deckman ............ A61F 6/144 128/833 |
| 2013/0192606 A1 | 8/2013 | Ziv et al. |
| 2013/0213406 A1* | 8/2013 | Frankenne ............ A61F 6/14 128/830 |
| 2015/0297392 A1 | 10/2015 | Karapasha |
| 2015/0305844 A1 | 10/2015 | Schuman et al. |
| 2016/0015500 A1 | 1/2016 | Ziv et al. |
| 2016/0220342 A1 | 8/2016 | Ziv et al. |
| 2016/0235583 A1 | 8/2016 | Durling et al. |
| 2016/0296379 A1 | 10/2016 | Brown et al. |
| 2016/0296380 A1 | 10/2016 | Graham et al. |
| 2016/0374788 A1 | 12/2016 | Ramachandra et al. |
| 2017/0014217 A1 | 1/2017 | Patrusky |
| 2017/0100278 A1 | 4/2017 | Ziv et al. |

\* cited by examiner

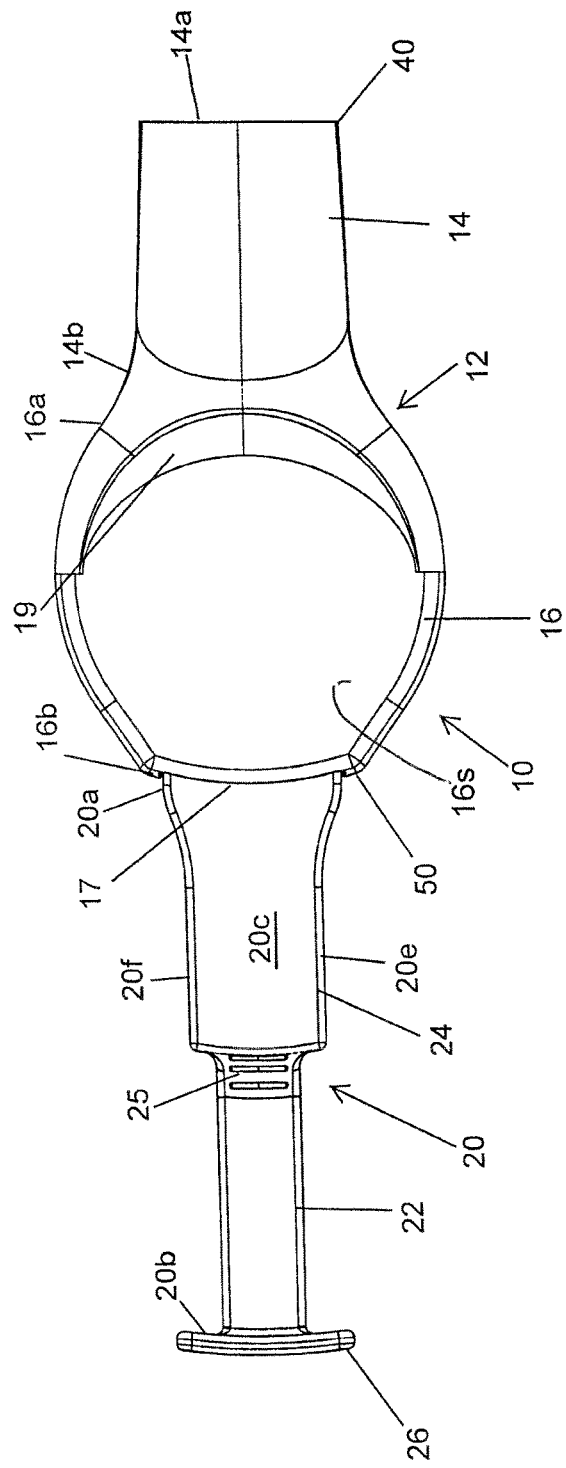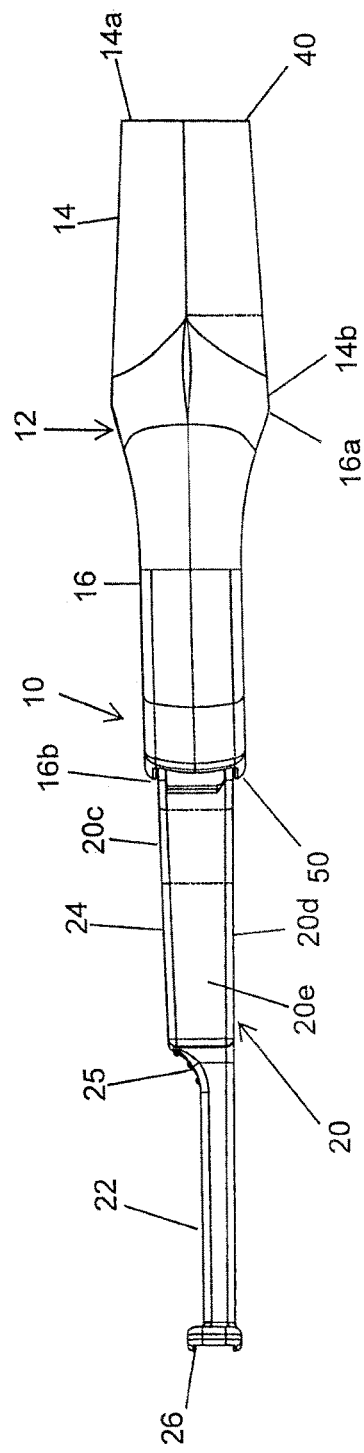
FIG. 3
FIG. 4

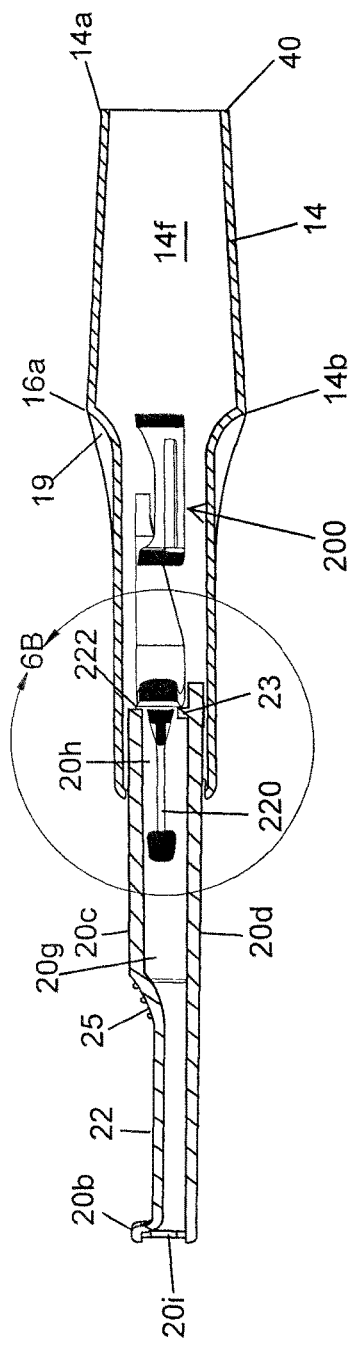
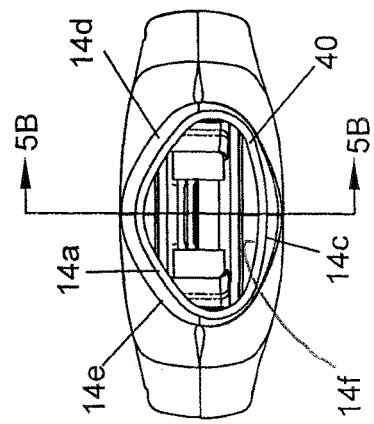
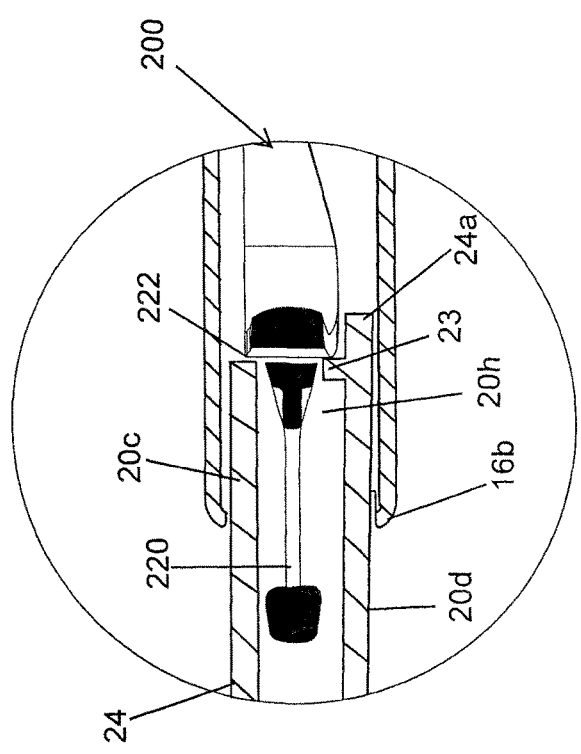
FIG. 5B
FIG. 7B
FIG. 6B

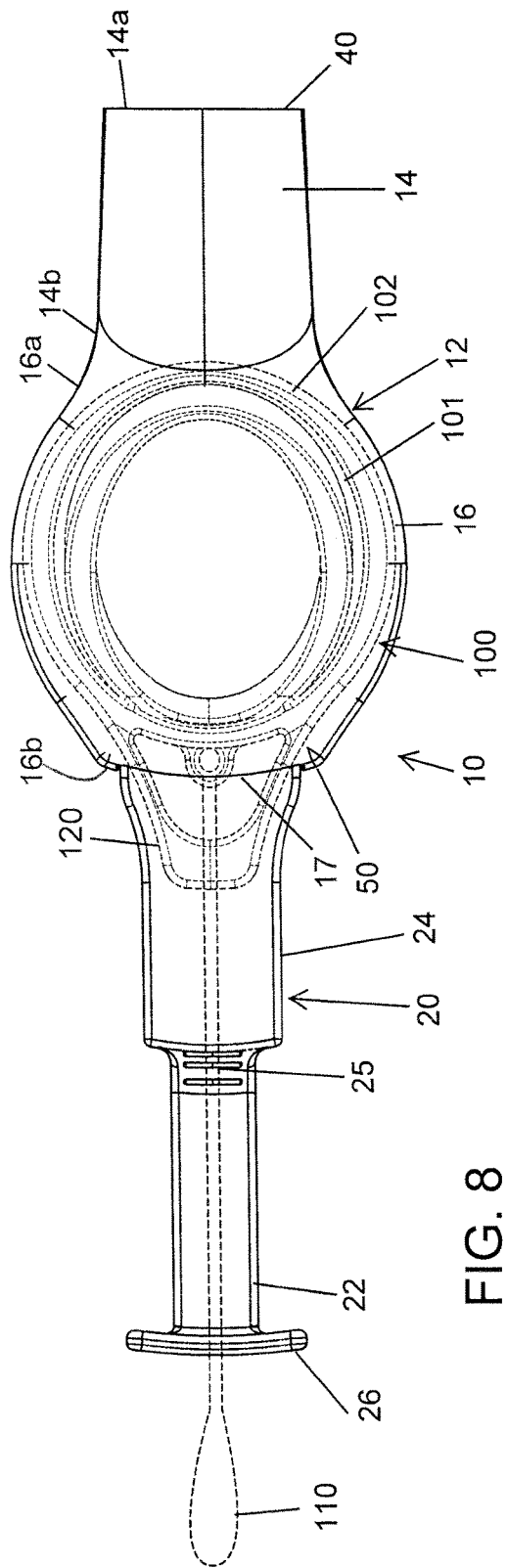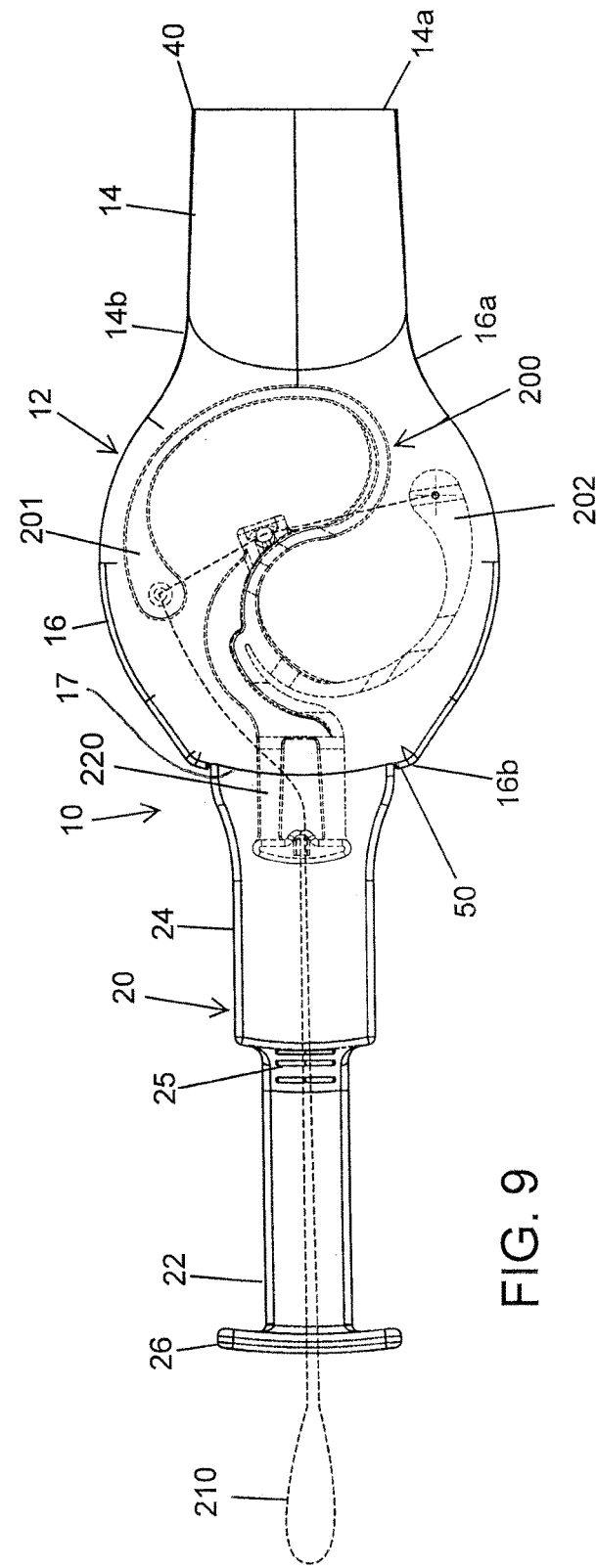

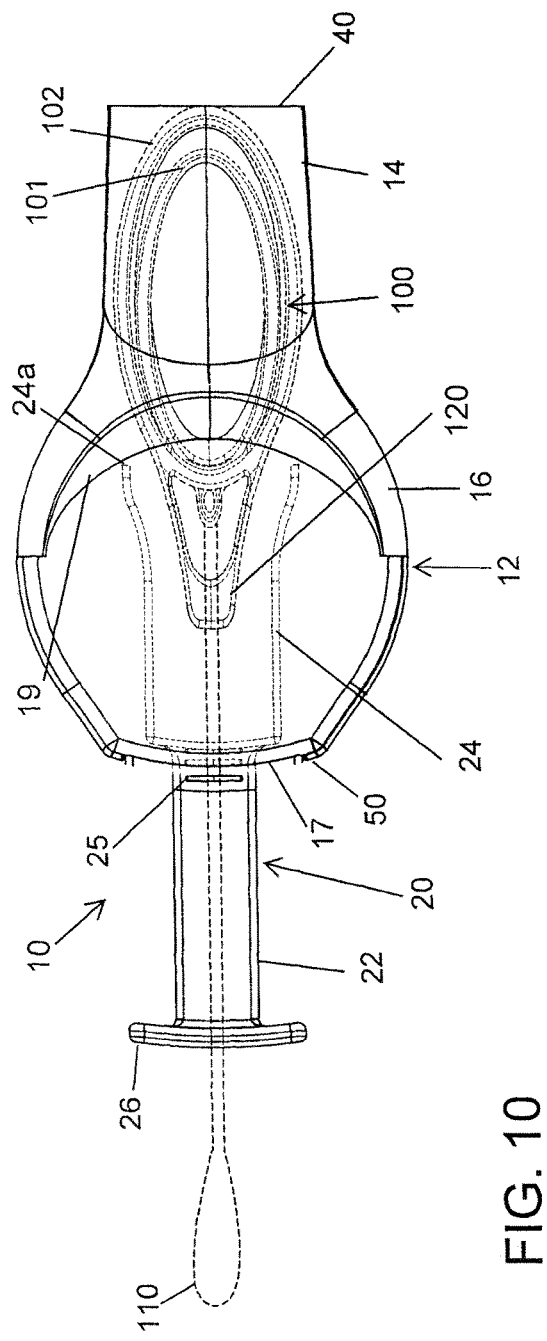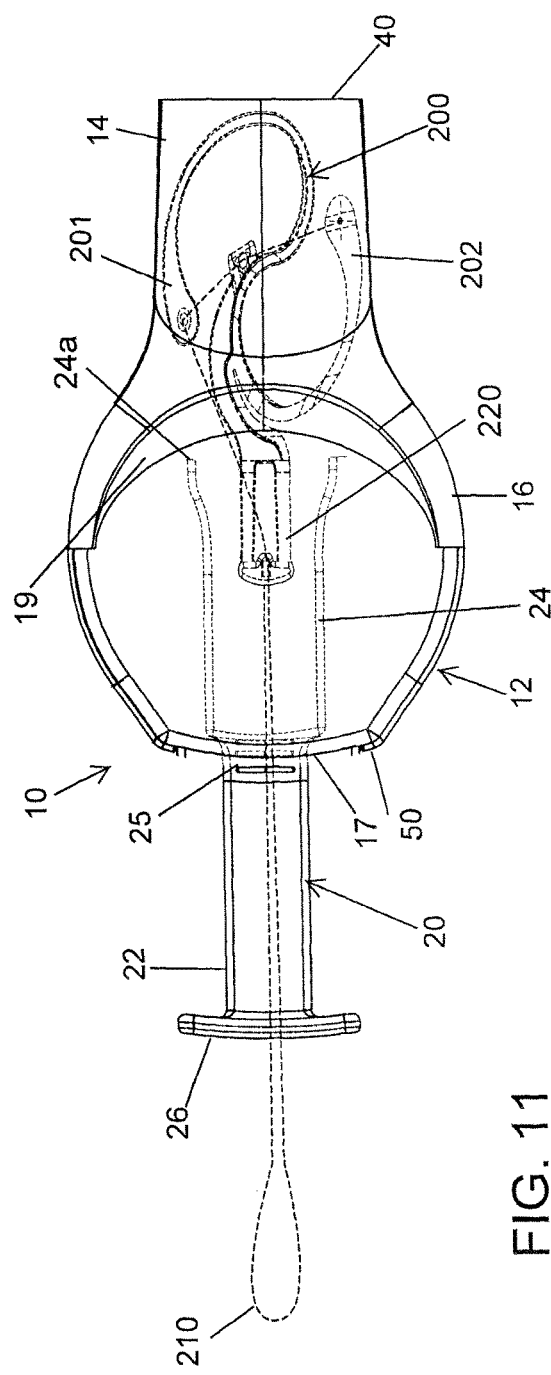

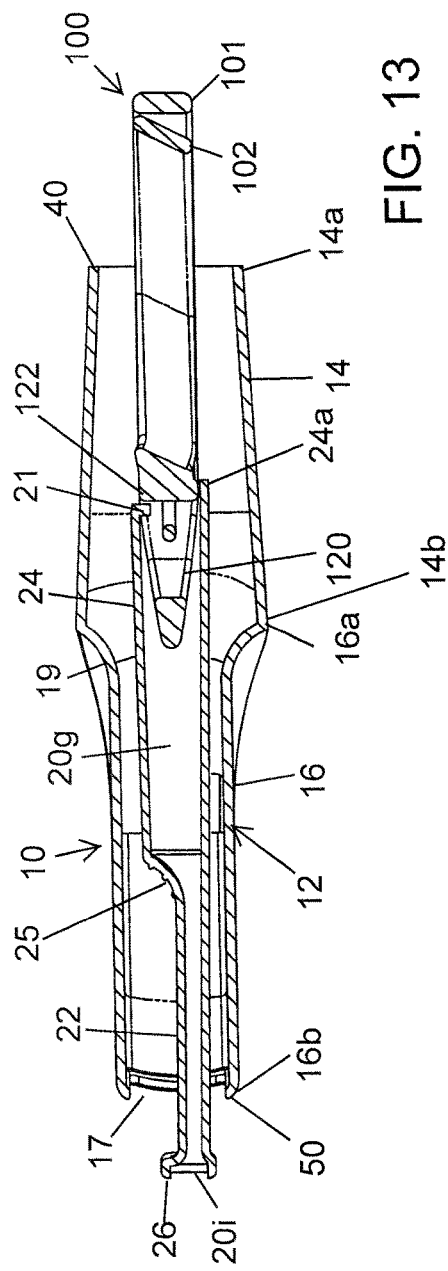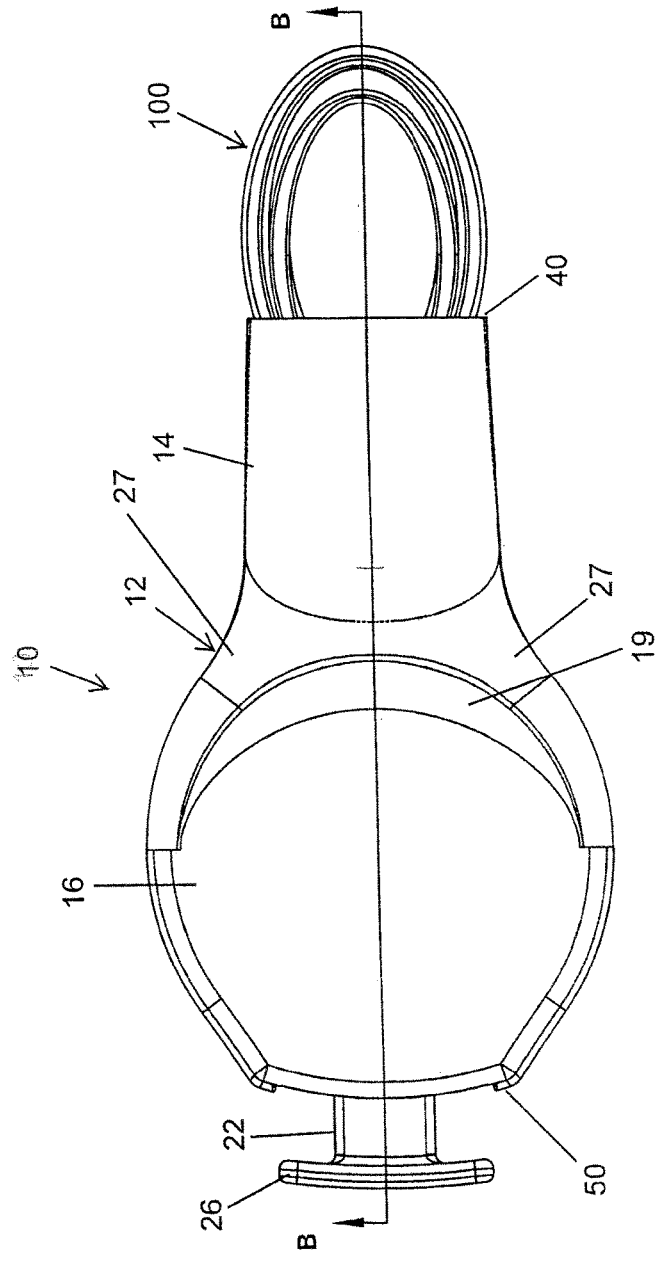

INTRODUCER FOR URINARY INCONTINENCE

CROSS REFERENCE TO RELATED APPLICATION

This application claims the benefit of U.S. Provisional Application Ser. No. 62/490,364, entitled "INTRODUCER FOR URINARY INCONTINENCE DEVICE," filed Apr. 26, 2017.

BACKGROUND OF THE INVENTION

1. Field of the Invention

The present invention generally relates to an introducer for a Urinary Incontinence (UI) device.

2. Description of the Related Art

By way of background, urinary incontinence is the involuntary leakage of urine; in simple terms, it means a person urinates when he or she does not want to. Control over the urinary sphincter is either lost or weakened.

SUMMARY OF THE INVENTION

It is, therefore, an object of the present invention to provide an introducer used to insert a urinary incontinence device into a vagina. The introducer includes a housing including a vaginal insertion tube at a proximal end of the housing and a storage section at a distal end of the housing. The storage section is shaped and dimensioned for storage of the urinary incontinence device prior to insertion and the vaginal insertion tube is shaped and dimensioned for the passage of the urinary incontinence device therethrough. The dimensions of the storage section are such that the urinary incontinence device contained therein is in its deployed non-compressed state allowing the urinary incontinence device to be stored in its non-compressed state prior to use. The introducer also includes a plunger which travels within the housing.

It is also an object of the present invention to provide an introducer used to insert a urinary incontinence device into a vagina including a housing having a vaginal insertion tube at a proximal end of the housing and a storage section at a distal end of the housing. The storage section is shaped and dimensioned for storage of the urinary incontinence device prior to insertion, while the vaginal insertion tube is shaped and dimensioned for the passage of the urinary incontinence device therethrough. The introducer also includes a plunger which travels within the housing. The plunger includes a top wall, a bottom wall, and lateral side walls extending between the top wall and the bottom wall. The top wall, bottom wall, and lateral side walls define an internal cavity extending from a proximal first end of the plunger for housing part of the urinary incontinence device.

It is another object of the present invention to provide an introducer used to insert a urinary incontinence device into a vagina including a housing having a vaginal insertion tube at a proximal end of the housing and a storage section at a distal end of the housing. The storage section is shaped and dimensioned for storage of the urinary incontinence device prior to insertion, while the vaginal insertion tube is shaped and dimensioned for the passage of the urinary incontinence device therethrough. The introducer also includes a plunger which travels within the housing. The plunger is an elongated member and includes a proximal first end and a distal second end with a handle secured thereto. The plunger includes a first plunger portion adjacent the distal second end thereof and a second plunger portion adjacent the proximal first end thereof with a gripping area at an intersection of the first plunger portion and the second plunger portion. The gripping area allows pushing of the plunger in two steps.

It is a further object of the present invention to provide a method of introducing a urinary incontinence device into a vagina. The method includes the steps of obtaining (for example, from a drug store) an introducer with a urinary incontinence device stored within a storage section of the introducer therein, inserting an insertion tube of the introducer within the vagina, pushing a plunger of the introducer to move the urinary incontinence device from the storage section of the housing into the insertion tube, and pushing the plunger farther to force the urinary incontinence device from the insertion tube and into the vagina wherein resilience of the urinary incontinence device forces the urinary incontinence device toward deployment once more than half of the urinary incontinence device is exposed.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 3 is a top view of the introducer shown in FIG. 1.

FIG. 4 is a side elevation view of the introducer shown in FIG. 1.

FIG. 5B is a cross-sectional view of the introducer taken along line 5B-5B shown in FIG. 7B.

FIG. 6B is an exploded view of area 6B in shown in FIG. 5B.

FIG. 7B is a proximal end cross-section view of the introducer shown in FIG. 1 with a second embodiment of a UI device contained therein.

FIG. 8 is a top view of the introducer shown in FIG. 1 with the plunger fully extended and including the first embodiment of a UI device shown in broken lines inside the introducer.

FIG. 9 is a top view of the introducer shown in FIG. 1 with the plunger fully extended and including the second embodiment of a UI device shown in broken lines inside the introducer.

FIG. 10 is a top view of the introducer shown in FIG. 8 with the plunger halfway compressed.

FIG. 11 is a top view of the introducer shown in FIG. 9 with the plunger halfway compressed.

FIG. 12 is a top view of the introducer shown in FIG. 8 with the plunger almost completely compressed.

FIG. 13 is a cross-sectional view of the introducer taken along line B-B in FIG. 12.

DESCRIPTION OF THE PREFERRED EMBODIMENTS

Figure 1:
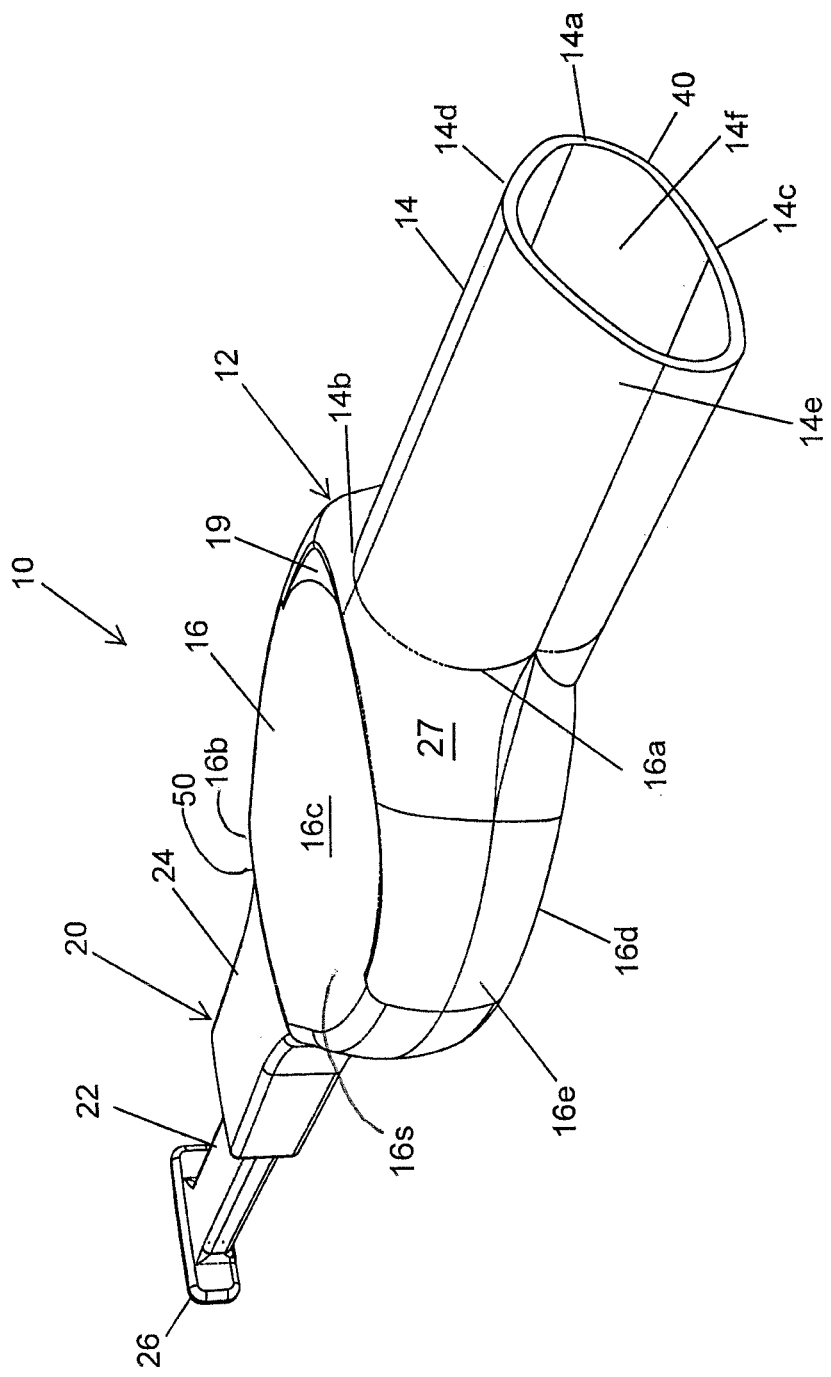
FIG. 1 a front perspective view of the introducer of the present invention.
Figure 2:
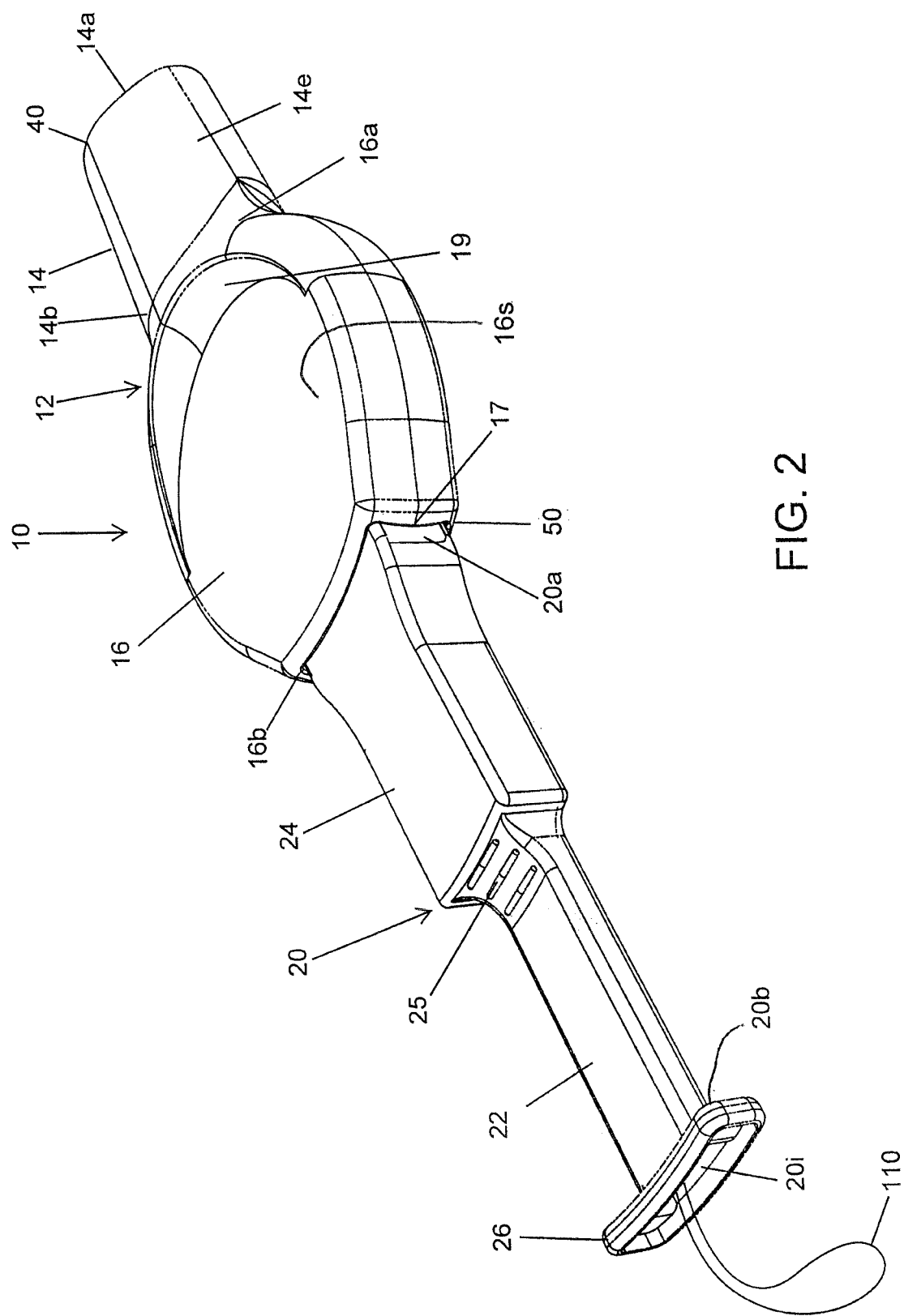
FIG. 2 is a rear perspective view of the introducer shown in FIG. 1.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring to FIGS. 1 to 15, the introducer 10 of the present invention is shown. The introducer 10 may be used to insert two different embodiments of UI devices 100, 200 into the vagina. In accordance with a preferred embodiment, the two different UI devices that may be used in accordance with the present invention are those disclosed in U.S. Patent Application Publication No. 2018/0021120, published Jan. 25, 2018, entitled "INCONTINENCE DEVICE," and U.S. Patent Application Publication No. 2018/0021121, published Jan. 25, 2018, entitled "INCONTINENCE DEVICE," both of which are incorporated herein by reference. The first embodiment of the UI device 100 is best viewed in FIG. 14 and the second embodiment of the UI device 200 is best viewed in FIG. 15. The UI devices 100, 200 are compressed by the introducer 10 during insertion into the vagina and then return to an expanded deployed state after complete insertion into the vagina.

The introducer 10 includes a housing 12 and a plunger 20 which travels within the housing 12. The housing 12 includes a proximal end 40 and a distal end 50. The housing 12 further includes a vaginal insertion tube 14 at the proximal section of the housing 12. The housing 12 also includes a storage section 16 at the distal section of the housing 12. The storage section 16 is shaped and dimensioned for storage of the UI device 100, 200 prior to insertion, while the vaginal insertion tube 14 is shaped and dimensioned for the passage of the UI device 100, 200 therethrough in a manner that will be discussed below in greater detail. As the UI device 100, 200 is stored within the storage section 16 and passed through the vaginal insertion tube 14, both the storage section 16 and the vaginal insertion tube 14 are hollow and they are in communication with each other such that the UI device 100, 200 may be passed from the storage section 16 into the vaginal insertion tube 14 and out of the housing 12.

The vaginal insertion tube 14 includes a proximal first end 14a which coincides with the proximal end 40 of the housing 12 and a distal second end 14b that is secured to the storage section 16. The vaginal insertion tube 14 is in the shape of a soft triangle and increases in size as it extends back from the proximal first end 14a toward the distal second end 14b and the storage section 16.

Figure 7A:
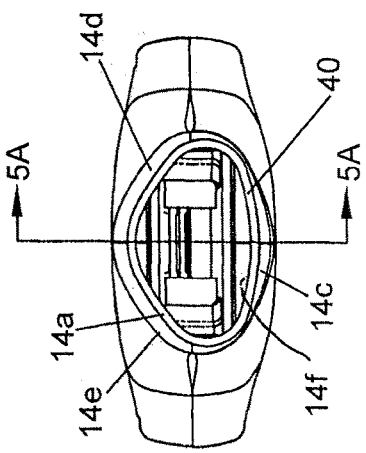
FIG. 7A is a proximal end view of the introducer shown in FIG. 1 with a first embodiment of a UI device contained therein.
Figure 6A:
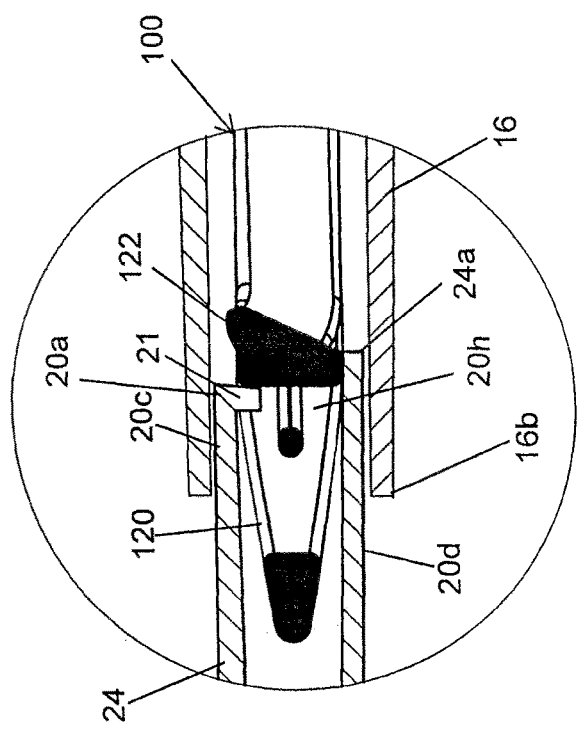
FIG. 6A is an exploded view of area 6A shown in FIG. 5A.

As mentioned above, the vaginal insertion tube 14 has the shape of a soft triangle or unique transitional shape other than oval. This means that when the vaginal insertion tube 14 is viewed along an axis aligned with the longitudinal axis of the housing 12 (see FIGS. 7A and 7B), the vaginal insertion tube 14 exhibits a triangular or unique transitional shaped as defined by a base wall 14c of the vaginal insertion tube 14, a left side wall 14d of the vaginal insertion tube 14, and a right side wall 14e of the vaginal insertion tube 14. As shown in FIGS. 7A and 7B, the intersection between the base wall 14c and the left side wall 14d is curved, the intersection between the base wall 14c and the right side wall 14e is curved, and the intersection between the left side wall 14d and right side wall 14e is curved, thus forming a soft triangle, that is a triangle in which the vertex are curved, not a point. The vaginal insertion tube 14 is hollow and the walls 14c, 14d, 14e define a passageway 14f shaped and dimensioned for the passage of the UI device 100, 200 therethrough in a manner that will be discussed below in greater detail. In accordance with a preferred embodiment, the passageway 14f defined by the vaginal insertion tube 14 is slightly larger than 1 inch along its largest width dimension, approximately 0.80 inches in its largest height dimension adjacent the distal second end 14b thereof, approximately 0.65 inches in its height dimension adjacent the proximal first end 14a thereof, and 1.5 inches in length as it extends from its proximal first end 14a to its distal second end 14b. While the soft triangle shape is the preferred embodiment it is contemplated other shapes could be used as long as they function to compress the UI device 100, 200 during insertion.

The storage section 16 is disc shaped and includes a proximal first end 16a (that is coupled to the distal second end 14b of the vaginal insertion tube 14) and a distal second end 16b (that coincides with the distal end 50 of the housing 12). The distal second end 16b of the storage section 16 is provided with an aperture 17 shaped and dimensioned for receiving the plunger 20 such that the plunger may be moved within the housing 12 in a manner discussed below in greater detail. The storage section 16 also includes an upper wall 16c, a lower wall 16d, and a side wall 16e extending between the upper wall 16c and the lower wall 16d.

The storage section 16 has a diameter of almost 2 inches. In addition, the storage section has a height of 0.80 inches adjacent the proximal first end 16a thereof and a height of 0.50 inches adjacent the distal second end 16b thereof. The transition in height from the proximal first end 16a to the distal second end 16b is not gradual. Rather, the transition is abrupt at the proximal first end 16a where the storage section goes from a height of 0.80 inches to a height of 0.50 inches over a very short distance to define a finger abutment surface 19 along the outer surface 16s of the storage section 16 adjacent the proximal first end 16a thereof. As will be appreciated as the operation of the present introducer 10 is explained, the finger abutment surface 19 allows a user to push the introducer 10 forward while holding the storage section 16 without worrying that fingers will slide onto the vaginal insertion tube 14 and inhibit insertion of the vaginal insertion tube 14 into the vagina.

Still further, the fact that the diameter of the storage section 16 is greater than the width dimension of the vaginal insertion tube 14 means that the storage section 16 extends laterally beyond the vaginal insertion tube 14. This lateral extension at the junction of the storage section 16 and the vaginal insertion tube 14 results in a vaginal abutment surface 27 along the proximal first end 16a of the storage section 16 that prevents the storage section 16 from entering the vagina when the vaginal insertion tube 14 is inserted into the vagina.

With the foregoing dimensions in mind, it is appreciated that the housing 12 increases in height from its distal end 50 until the intersection of the vaginal insertion tube 14 and the storage section 16 and then decreases in height as it extends proximally to proximal end 40 (that is, from the distal second end 16b of the storage section 16 to the proximal first end 16a of the storage section 16 the housing 12 increases in height and from the distal second end 14b of the vaginal insertion tube 14 to the proximal first end 14a of the vaginal insertion tube 14 the housing 12 decreases in height). The increasing height functions to guide the compression of the UI device 100, 200 as it is pushed proximally (that is, toward the proximal first end 14a of the vaginal insertion tube 14) by the plunger 20. The increase in height also helps to minimize the pushing force required on the plunger 16 to start the travel of the UI device 100, 200 proximally. The dimensions of storage section 16 are such that the UI device 100, 200 contained therein is in its deployed orientation, that is, it is in its non-compressed state. This allows the UI device 100, 200 to be stored in its non-compressed state prior to use, thus not affecting its performance after being stored for long periods of time prior to introduction. With this in mind, it should be appreciated the term "non-compressed state" is meant to refer to the UI device 100, 200 when it is not compressed sufficiently to pass through the vaginal insertion tube 14. As such, and while the UI device 100, 200 is held in the storage section 16 it is either fully extended or it is slightly constricted in a manner not adversely affecting its long-term viability. With the foregoing in mind, it is considered the UI device 100, 200 is in its compressed state when it has been reduced to a size sufficient to pass through the vaginal insertion tube 14 and it is in its non-compressed state when it is too large to pass through the vaginal insertion tube (and is not adversely affected with regard to its long-term viability).

Also the size of the storage section 16 provides a generous gripping area for a user. With this in mind, it is appreciated the storage section 16 may be provided with a tactile grip pattern on the exterior thereof (not shown). Preferably the housing 12 is made from a plastic such as polypropylene or polyethylene, but other materials could be used.

The UI devices 100, 200 are stored within the storage section 16 of the housing 12 of the introducer 10 in their expanded or non-compressed state and during insertion are compressed as they pass within vaginal insertion tube 14. In accordance with the embodiment disclosed with reference to FIGS. 1-15, the vaginal insertion tube 14 has a completely open end at its proximal first end 14a. However, and in accordance with the alternate embodiment disclosed with reference to FIG. 16, the proximal first end 14a of the vaginal insertion tube 14 is partially covered by an array of curved flexible petals (or flaps) 18 as shown in FIG. 16.

The plunger 20 is an elongated member and includes a proximal first end 20a and a distal second end 20b with a handle 26 secured thereto. The plunger 20 is hollow and includes a top wall 20c, a bottom wall 20d, and lateral side walls 20e, 20f extending between the top wall 20c and the bottom wall 20d. The top wall 20c, bottom wall 20d, and lateral side walls 20e, 20f define an internal cavity 20g extending from a first opening 20h at the first end 20a of the plunger 20 to a second opening 20i at the distal second end 20b of the plunger 20. The internal cavity 20g allows a cord 110, 210 connected to the UI device 100, 200 to pass through the plunger 20 (that is, pass through the first opening 20h at the first end 20a of the plunger 20, the internal cavity 20g, and the second opening 20i at the second end of the plunger 20) and exit the plunger 20 at the second end 20b thereof. Preferably the plunger 20 is made from a plastic such as polypropylene or polyethylene, or paper, but other materials could be used.

Figure 5A:
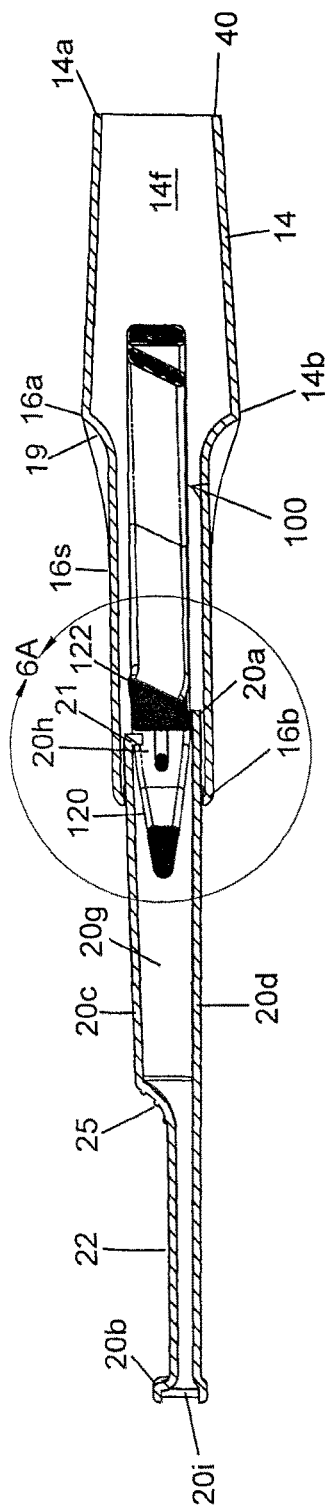
FIG. 5A is a cross-sectional view of the introducer taken along line 5A-5A shown in FIG. 7A.

The plunger 20 includes a first plunger portion 22 adjacent the distal second end 20b thereof and a second plunger portion 24 adjacent the proximal first end 20a thereof. The first plunger portion 22 and the second plunger portion 24 together have a length slightly less than 4 inches. The first plunger portion 22 is longer than the second plunger portion 24 and is at the maximum comfortable reach for a typical user. The overall length of the plunger 20 is greater than the overall length of the housing 12. The internal cavity 20g of plunger 20 that sits within the second plunger portion 24 is dimensioned to house part of the UI device 100, 200 to minimize the size of storage section 16. In particular, it is dimensioned to house the tab 120, 220 of the UI device 100, 200. This is best seen in FIGS. 5A and 8 for UI device 100 and 5B and 9 for UI device 200.

The first proximal end 20a of the plunger 20, that is, the free end 24a of the second plunger portion 24 is also in contact with the UI device 100, 200 to push it forward during insertion of the UI device 100, 200 into the vagina. In particular, each of the UI devices 100, 200 includes an abutment surface 122, 222 that is slightly larger in height than the opening defined by the top wall 20c and the bottom wall 20d of the plunger 20 at the free end 24a of the second plunger portion 24. As a result, the free end 24a of the second plunger portion 24 engages the abutment surface 122, 222 of the UI devices 100, 200 in a manner allowing the plunger 20 to push the UI devices 100, 200 forward as the plunger 20 is moved forward.

In accordance with a first embodiment as shown with reference to FIGS. 5A, 6A, 7A and 8, which is particularly suited for UI device 100, engagement between the free end 24a of the second plunger portion 24 and the abutment surface 122 of the UI device 100 is further enhanced by structuring the top wall 20c and the bottom wall 20d at the free end 24a of the second plunger portion 24 such that the bottom wall 20d extends farther than the top wall 20c and the top wall 20c includes a downwardly extending flange 21. In this way the abutment surface 122 sits upon the bottom wall 20d while the flange 21 extending downwardly from the top wall 20c abuts the abutment surface 122 to move the UI device 100 forward as the plunger 20 is moved forward.

In accordance with an alternate embodiment as shown in FIGS. 5B, 6B, 7B and 9, which is particularly suited for UI device 200, engagement between the free end 24a of the second plunger portion 24 and the abutment surface 222 of the UI device 200 is enhanced by structuring the top wall 20c and the bottom wall 20d at the free end 24a of the second plunger portion 24 such that the bottom wall 20d extends farther than the top wall 20c and the bottom wall 20d includes an upwardly extending flange 23 in alignment with the edge of the top wall 20c. In this way the abutment surface 222 sits upon the bottom wall 20d while the edge of the top wall 20c and the flange 23 extending upwardly from the bottom wall 20d abut the abutment surface 222 to move the UI device 200 forward as the plunger 20 is moved forward.

At the intersection of first plunger portion 22 and second plunger portion 24 is a gripping area 25. The gripping area 25 allows pushing of the plunger 20 in two steps. A user first contacts the gripping area 25 and pushes the second plunger portion 24 into housing 12 until her finger(s) abuts the distal end 50 of the housing 12. Thereafter, the user contacts the handle 26 and continues to push the first plunger portion 22 into the housing 12 until the handle 26 abuts the distal end 50 of housing 12. The two-step insertion permits the introducer 10 to be used by women with varying dexterity, hand strength, and hand size. The two steps provide optimal location of the "press areas" at all times during use for most, if not all, users. The length of the housing 12 and plunger 20 are longer due to the functional size needed to store the UI device in a non-compressed state.

Turning to FIGS. 8, 10, 12, 13, and 14, the operation of introducer 10 will be described. As seen in FIG. 8, the UI device 100 is shown in broken lines stored within the storage section 16 of the housing 12. The UI device 100 is stored in a non-compressed state. Accordingly, the small second ring portion 102 of UI device 100 is not in contact with the interior 15 of housing 12.

As seen in FIG. 10, the second plunger portion 24 has been pressed to fully reside within the housing 12, and the gripping area 25 is adjacent the distal end 50 of the housing 12. The UI device 100 has been pushed into insertion tube 14. In this position, the small second ring portion 102 of the UI device 100 is compressed into the large first ring portion 101 of the UI device 100 and is in contact with the interior 15 of the housing 12.

Figure 14:
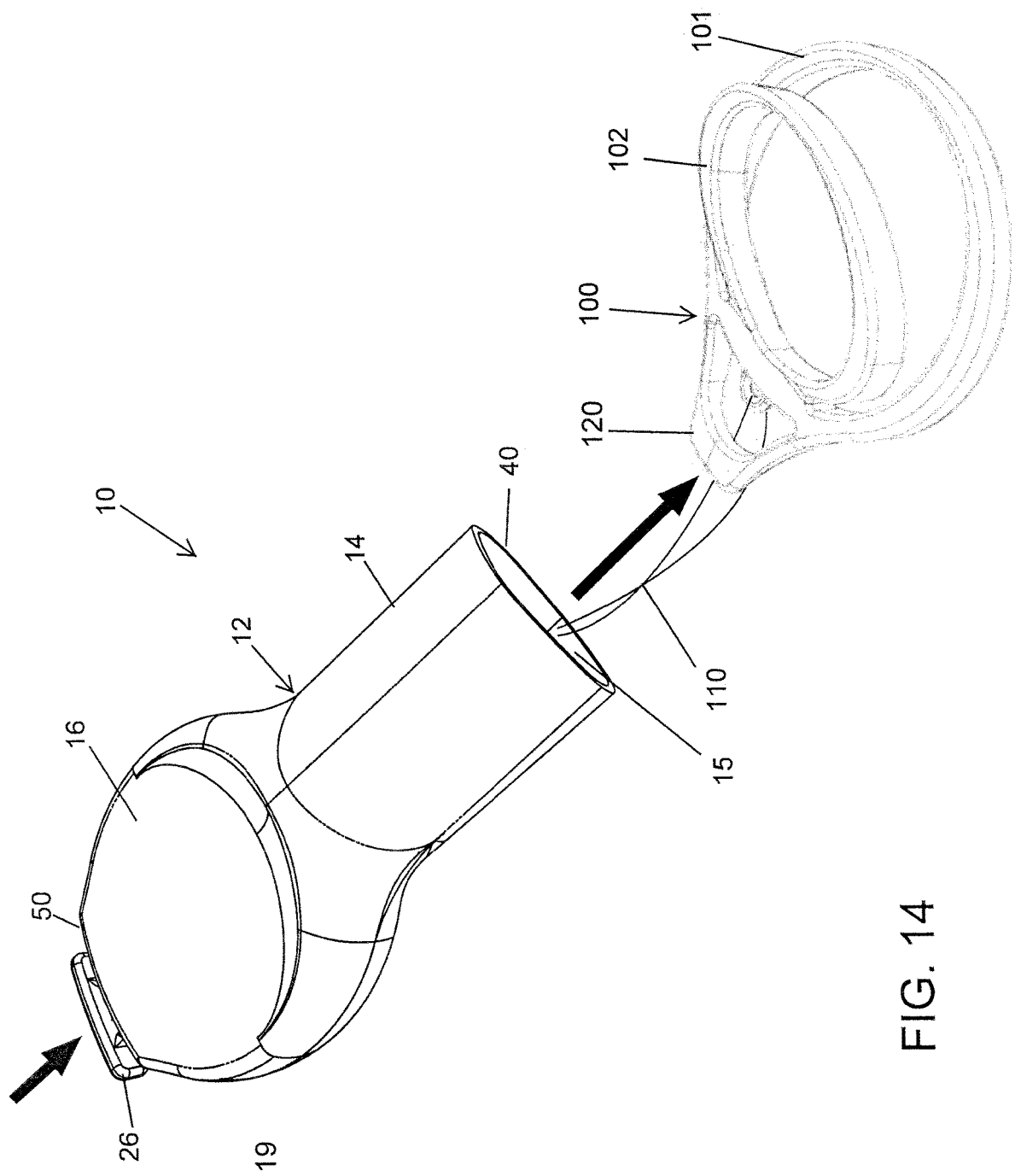
FIG. 14 is a front perspective view of the introducer shown in FIG. 8 with the plunger fully compressed and the UI device deployed outside of the introducer.

Next, and as seen in FIGS. 12 and 13, the first plunger portion 22 is almost fully pressed to reside within housing 12 and UI device 100 begins to exit insertion tube 14 at the proximal end 40 of the housing 12. Lastly, and as seen in FIG. 14, the handle 26 is about to abut the distal end 50 of the housing 12 and the UI device 100 has fully exited the introducer 10. Deployment of the UI device 100 is assisted by the shape and resilience of the UI device 100 since the resilience of the UI device 100 will force the UI device 100 toward deployment once more than half of the UI device 100 is exposed. Upon exiting the introducer, the UI device 100 would be properly positioned within the vagina with cord 110 extending outside of the vagina. In this position, portions 101 and 102 of UI device 100 expand away from each other and the UI device 100 is in its deployed state. Cord 110 extends outside the vagina so that when it is desired to remove the UI device 100 the cord 110 may be pulled to collapse small second ring portion 102 into larger first ring portion 101 of the UI device 100 and then continued to be pulled until the UI device 100 exits the vagina.

Figure 15:
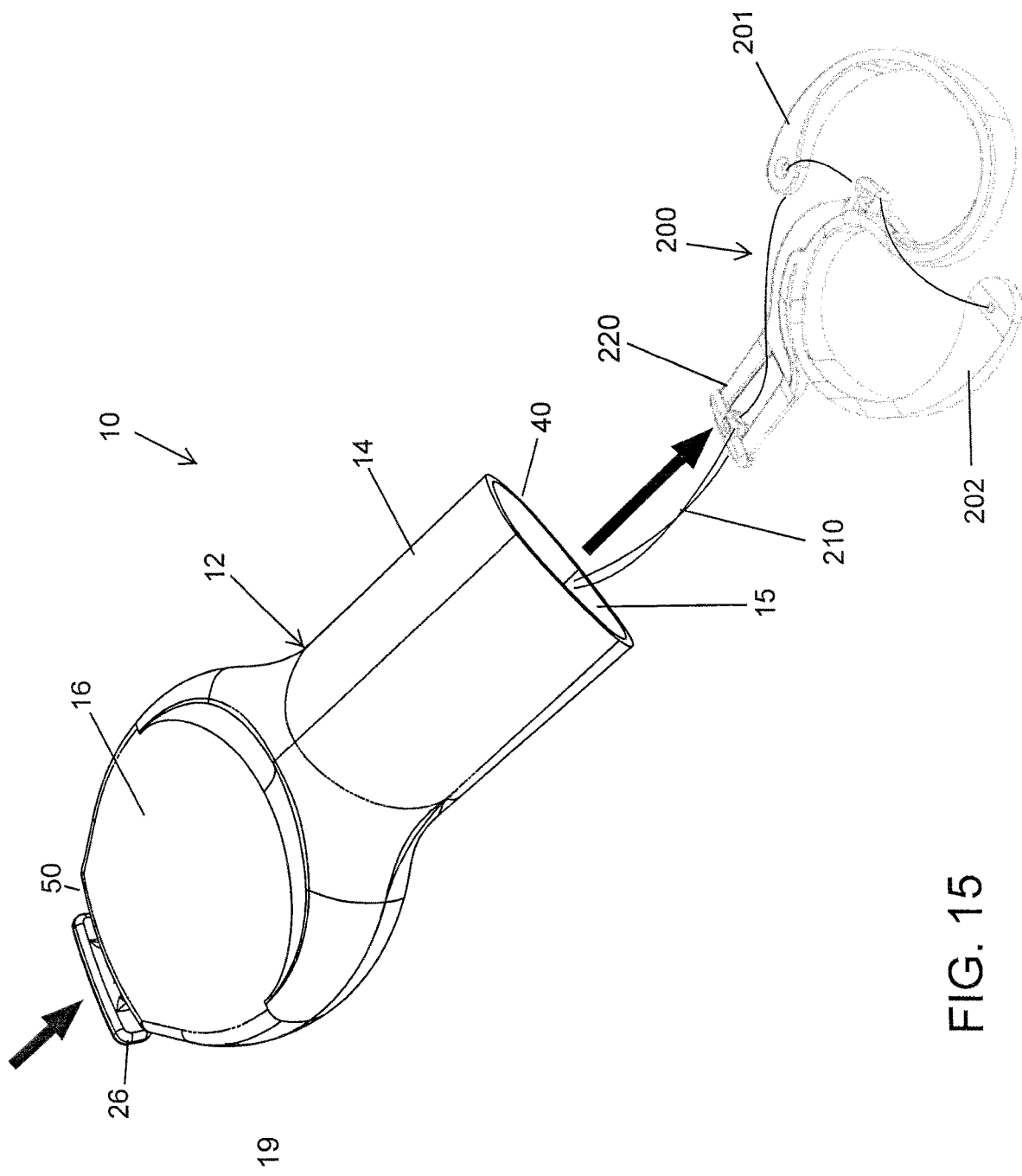
FIG. 15 is a front perspective view of the introducer shown in FIG. 9 with the plunger fully compressed and the UI device deployed outside of the introducer.
Figure 16:
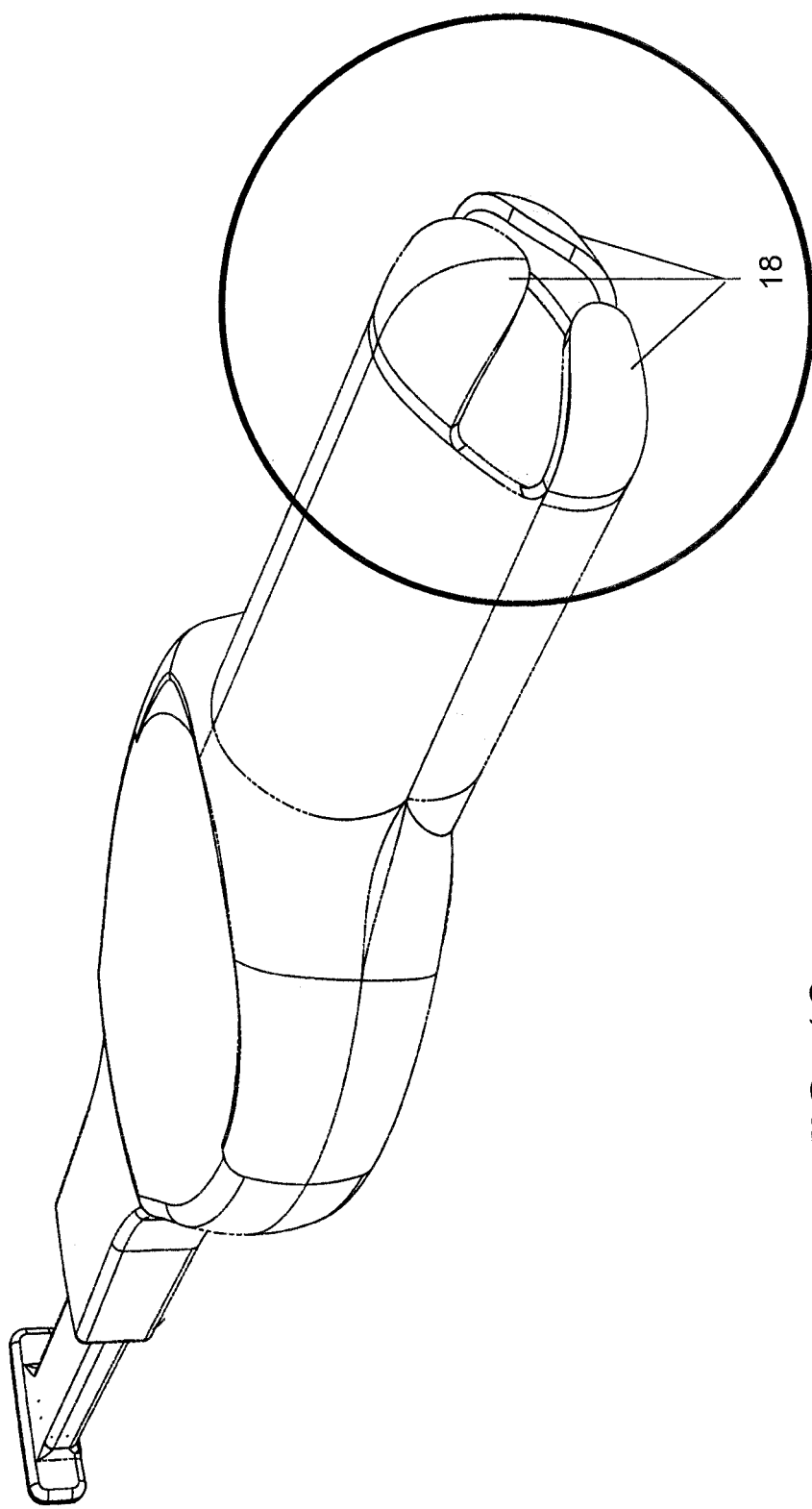
FIG. 16 is a front perspective view of a second embodiment of the introducer including petals at the discharge opening.

Similar, and with reference to FIGS. 9, 11 and 15, the second embodiment of the UI device 200 is shown as it is introduced. As seen in FIG. 9, the UI device 200 is shown in broken lines stored within the storage section 16 of the housing 12. The UI device 200 is stored in a non-compressed or semi-compressed state. Accordingly, first arcuate arm portion 201 and second arcuate arm portion 202 of the UI device 200 are not in contact with the interior 15 of the housing 12. As seen in FIG. 11, the second plunger portion 24 has been pressed to fully reside within the housing 12, the gripping area 25 is adjacent the distal end 50 of the housing 12 and the UI device 200 has been pushed into the insertion tube 14. In this position, first arcuate arm portion 201 and second arcuate arm portion 202 of UI device 200 are compressed and in contact with the interior 15 of the housing 12. Lastly, and as seen in FIG. 15, the handle 26 is about to abut the distal end 50 of the housing 12 and the UI device 200 has fully exited the introducer 10. Upon exiting the introducer 10, the UI device 200 would be properly positioned within the vagina with cord 210 extending outside of the vagina. In this position, portions 201 and 202 of the UI device 200 expand away from each other and the UI device 200 is in its deployed state. Cord 210 extends outside the vagina so that when it is desired to remove the UI device 200 the cord 210 may be pulled to draw first arcuate arm portion 201 closer to second arcuate arm portion 202 of the UI device 200. Cord 210 may then continue to be pulled until the UI device 200 exits the vagina.

While the preferred embodiments have been shown and described, it will be understood that there is no intent to limit the invention by such disclosure, but rather, it is intended to cover all modifications and alternate constructions falling within the spirit and scope of the invention.

The invention claimed is:

1. An introducer used to insert a urinary incontinence device into a vagina, comprising:
   a housing including a vaginal insertion tube at a proximal end of the housing and a storage section at a distal end of the housing, the storage section is shaped and dimensioned for storage of the urinary incontinence device prior to insertion and the vaginal insertion tube is shaped and dimensioned to contact the urinary incontinence device and reduce the urinary incontinence device to a size sufficient for the passage of the urinary incontinence device therethrough in a compressed state, wherein dimensions of the storage section are such that the urinary incontinence device contained therein is in its deployed non-compressed state allowing the urinary incontinence device to be stored in its non-compressed state prior to use, the vaginal insertion tube including a proximal first end and a distal second end that is secured to the storage section, and the storage section and the vaginal insertion tube are in communication with each other such that the urinary incontinence device may be passed from the storage section into the vaginal insertion tube and out of the housing, wherein a diameter of the storage section is greater than a width dimension of the vaginal insertion tube, and a changing shape of the storage section adjacent the distal second end of the vaginal insertion tube causes the urinary incontinence device to transition from the non-compressed state to the compressed state; and
   a plunger which travels within the housing, wherein the plunger travels through the storage section to push the urinary incontinence device into the vaginal insertion tube such that the urinary incontinence device becomes compressed before the urinary incontinence device is deployed.

2. The introducer according to claim 1, further including a urinary incontinence device stored in the storage section.

3. The introducer according to claim 2, wherein both the storage section and the vaginal insertion tube are hollow, wherein the urinary incontinence device is in the deployed non-compressed state when in the storage section, is in a compressed state as it passes through the vaginal insertion tube, and returns to the deployed non-compressed state upon deployment from the vaginal insertion tube.

4. The introducer according to claim 3, wherein an entirety of the urinary incontinence device is compressed as it passes through the vaginal insertion tube.

5. The introducer according to claim 4, wherein the storage section is disc shaped and includes a proximal first end and a distal second end, the distal second end of the storage section is provided with an aperture shaped and dimensioned for receiving the plunger such that the plunger may be moved within the housing.

6. The introducer according to claim 4, wherein the diameter of the storage section is greater than the width dimension of the vaginal insertion tube resulting in a vaginal abutment surface along the proximal first end of the storage section that prevents the storage section from entering the vagina when the vaginal insertion tube is inserted into the vagina.

7. The introducer according to claim 1, wherein the plunger includes a top wall, a bottom wall, and lateral side walls extending between the top wall and the bottom wall, the top wall, bottom wall, and lateral side walls defining an internal cavity extending from a proximal first end of the plunger for housing part of the urinary incontinence device.

8. The introducer according to claim 1, wherein the storage section is disc shaped and includes a proximal first end and a distal second end, the distal second end of the storage section is provided with an aperture shaped and dimensioned for receiving the plunger such that the plunger may be moved within the housing.

9. The introducer according to claim 8, further including a finger abutment surface along an outer surface of the storage section adjacent the proximal first end thereof, wherein the finger abutment surface allows a user to push the introducer forward while holding the storage section without worrying that fingers will slide onto the vaginal insertion tube and inhibit insertion of the vaginal insertion tube into the vagina.

10. The introducer according to claim 1, wherein the housing increases in height from its distal end until the intersection of the vaginal insertion tube and the storage section, and then decreases in height as it extends proximally to its proximal end, wherein this change in height guides compression of the urinary incontinence device as it is pushed proximally by the plunger and minimizes pushing force required on the plunger to start travel of the urinary incontinence device proximally.

11. An introducer used to insert a urinary incontinence device into a vagina, comprising:
   a housing including a vaginal insertion tube at a proximal end of the housing and a storage section at a distal end of the housing, wherein the storage section is shaped and dimensioned for storage of the urinary incontinence device in a non-compressed state prior to insertion, while the vaginal insertion tube is shaped and dimensioned to contact the urinary incontinence device and reduce the urinary incontinence device to a size sufficient for the passage of the urinary incontinence device therethrough in a compressed state, the vaginal insertion tube including a proximal first end and a distal second end that is secured to the storage section, and the storage section and the vaginal insertion tube are in communication with each other such that the urinary incontinence device may be passed from the storage section into the vaginal insertion tube and out of the housing, wherein a diameter of the storage section is greater than a width dimension of the vaginal insertion tube, and a changing shape of the storage section adjacent the distal second end of the vaginal insertion tube causes the urinary incontinence device to transition from the non-compressed state to the compressed state; and
   a plunger which travels within the housing, the plunger including a top wall, a bottom wall, and lateral side walls extending between the top wall and the bottom wall, the top wall, bottom wall, and lateral side walls defining an internal cavity extending from a proximal first end of the plunger for housing part of the urinary incontinence device, wherein the plunger travels through the storage section to push the urinary incontinence device into the vaginal insertion tube such that the urinary incontinence device becomes compressed before the urinary incontinence device is deployed.

12. The introducer according to claim 11, further including a urinary incontinence device stored in the storage section.

13. The introducer according to claim 12, wherein dimensions of the storage section are such that the urinary incontinence device contained therein is in its deployed non-compressed state allowing the urinary incontinence device to be stored in its non-compressed state prior to use, and wherein both the storage section and the vaginal insertion tube are hollow, wherein the urinary incontinence device is in the deployed non-compressed state when in the storage section, is in the compressed state as it passes through the vaginal insertion tube, and returns to the non-compressed state upon deployment from the vaginal insertion tube.

14. The introducer according to claim 11, wherein the plunger is an elongated member and includes a proximal first end and a distal second end with a handle secured thereto, the plunger includes a first plunger portion adjacent the distal second end thereof and a second plunger portion adjacent the proximal first end thereof.

15. The introducer according to claim 14, wherein the second plunger portion includes the top wall and the bottom wall at a free end of the second plunger portion, and the bottom wall extends farther than the top wall and the top wall includes a downwardly extending flange.

16. The introducer according to claim 14, wherein the second plunger portion includes the top wall and the bottom wall at a free end of the second plunger portion, and the bottom wall extends farther than the top wall and the bottom wall includes an upwardly extending flange in alignment with an edge of the top wall.

17. The introducer according to claim 14, further including a gripping area at an intersection of the first plunger portion and the second plunger portion.

18. The introducer according to claim 11, further including a cord connected to the urinary incontinence device and passing through the plunger.

19. An introducer used to insert a urinary incontinence device into a vagina, comprising:
   a housing including a vaginal insertion tube at a proximal end of the housing and a storage section at a distal end of the housing, wherein the storage section is shaped and dimensioned for storage of the urinary incontinence device in a non-compressed state prior to insertion, while the vaginal insertion tube is shaped and dimensioned to contact the urinary incontinence device and reduce the urinary incontinence device to a size sufficient for the passage of the urinary incontinence device therethrough in a compressed state, the vaginal insertion tube including a proximal first end and a distal second end that is secured to the storage section, and the storage section and the vaginal insertion tube are in communication with each other such that the urinary incontinence device may be passed from the storage section into the vaginal insertion tube and out of the housing, wherein a diameter of the storage section is greater than a width dimension of the vaginal insertion tube, and a changing shape of the storage section adjacent the distal second end of the vaginal insertion tube causes the urinary incontinence device to transition from the non-compressed state to the compressed state; and
   a plunger which travels within the housing, the plunger is an elongated member and includes a proximal first end and a distal second end with a handle secured thereto, the plunger including a first plunger portion of a first dimension adjacent the distal second end thereof and a second plunger portion of a second dimension different from the first dimension adjacent the proximal first end thereof with a gripping area at an intersection of the first plunger portion and the second plunger portion, the gripping area allowing pushing of the plunger in two steps, wherein the plunger travels through the storage section to push the urinary incontinence device into the vaginal insertion tube such that the urinary incontinence device becomes compressed before the urinary incontinence device is deployed.

20. The introducer according to claim 19, further including a urinary incontinence device stored in the storage section.

21. The introducer according to claim 20, wherein dimensions of the storage section are such that the urinary incontinence device contained therein is in its deployed non-compressed state allowing the urinary incontinence device to be stored in its non-compressed state prior to use, and wherein both the storage section and the vaginal insertion tube are hollow, wherein the urinary incontinence device is in the deployed non-compressed state when in the storage section, is in the compressed state as it passes through the vaginal insertion tube, and returns to the non-compressed state upon deployment from the vaginal insertion tube.

22. A method of introducing a urinary incontinence device into a vagina, comprising:
   obtaining an introducer with a urinary incontinence device in a non-compressed state stored within a storage section of the introducer therein;
   inserting an insertion tube of the introducer within the vagina;
   pushing a plunger of the introducer to move the urinary incontinence device from the storage section of a housing into contact with the insertion tube to compress the urinary incontinence device and reduce the urinary incontinence device to a size sufficient to fit within the insertion tube as the plunger moves the urinary incontinence device from the storage section of the housing into the insertion tube, the insertion tube including a proximal first end and a distal second end that is secured to the storage section, and the storage section and the insertion tube are in communication with each other such that the urinary incontinence device may be passed from the storage section into the insertion tube and out of the housing, wherein a diameter of the storage section is greater than a width dimension of the insertion tube, and a changing shape of the storage section adjacent the distal second end of the insertion tube causes the urinary incontinence device to transition from the non-compressed state to the compressed state; and
   pushing the plunger farther to force the urinary incontinence device from the insertion tube and into the vagina, wherein resilience of the urinary incontinence device forces the urinary incontinence device toward deployment once more than half of the urinary incontinence device is exposed.

* * * * *